(12) United States Patent
Gregg et al.

(10) Patent No.: US 8,808,161 B2
(45) Date of Patent: Aug. 19, 2014

(54) REDUNDANT TEMPERATURE MONITORING IN ELECTROSURGICAL SYSTEMS FOR SAFETY MITIGATION

(75) Inventors: William N. Gregg, Superior, CO (US); Derek M. Blaha, Longmont, CO (US)

(73) Assignee: Covidien AG (CH)

( * ) Notice: Subject to any disclaimer, the term of this patent is extended or adjusted under 35 U.S.C. 154(b) by 2176 days.

(21) Appl. No.: 10/573,210

(22) PCT Filed: Oct. 23, 2003

(86) PCT No.: PCT/US03/33832
§ 371 (c)(1),
(2), (4) Date: Jan. 16, 2007

(87) PCT Pub. No.: WO2005/048809
PCT Pub. Date: Jun. 2, 2005

(65) Prior Publication Data
US 2007/0203481 A1    Aug. 30, 2007

(51) Int. Cl.
*A61B 18/18*    (2006.01)
(52) U.S. Cl.
USPC ............................................. 600/34; 606/32
(58) Field of Classification Search
USPC .......................................... 606/32–38, 45–52
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,536,271 A | 1/1951 | Fransen et al. |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |

(Continued)

FOREIGN PATENT DOCUMENTS

| | | |
|---|---|---|
| CA | 1 219642 | 3/1987 |
| DE | 179607 | 3/1905 |

(Continued)

OTHER PUBLICATIONS

International Search Report PCT/US03/33832 Dated Jun. 11, 2004.

(Continued)

*Primary Examiner* — Linda Dvorak
*Assistant Examiner* — Amanda Scott

(57) ABSTRACT

A redundant temperature monitoring system and method for an electrosurgical system are provided. The temperature monitoring circuit includes at least one temperature sensor for sensing a temperature at a measuring point, a first temperature measurement circuit coupled to the at least one temperature sensor for generating a first temperature value, a second temperature measurement circuit coupled to the at least one temperature sensor for generating a second temperature value, and a control circuit for determining a difference between the first and second temperature values and for comparing the difference to a first predetermined threshold. If the difference is greater than the first predetermined threshold, the control circuit generates a warning signal. If the difference is greater than a second predetermined threshold, the control circuit generates an alarm signal and/or shuts down a power source of the electrosurgical system.

30 Claims, 4 Drawing Sheets

(56) References Cited

U.S. PATENT DOCUMENTS

| | | |
|---|---|---|
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,543,760 A | 12/1970 | Bolduc |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,812,861 A | 5/1974 | Peters |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 3,987,796 A | 10/1976 | Gonser |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,067,342 A | 1/1978 | Burton |
| 4,074,719 A | 2/1978 | Semm |
| 4,092,985 A | 6/1978 | Kaufman |
| 4,092,986 A | 6/1978 | Schneiderman |
| 4,094,320 A | 6/1978 | Newton et al. |
| 4,102,341 A | 7/1978 | Ikuno et al. |
| 4,114,622 A | 9/1978 | Gonser |
| 4,114,623 A | 9/1978 | Meinke et al. |
| 4,117,846 A | 10/1978 | Williams |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,166,465 A | 9/1979 | Esty et al. |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,213,463 A | 7/1980 | Osenkarski |
| 4,231,372 A | 11/1980 | Newton |
| 4,232,676 A | 11/1980 | Herczog |
| 4,237,887 A | 12/1980 | Gonser |
| 4,237,891 A | 12/1980 | DuBose et al. |
| 4,253,721 A | 3/1981 | Kaufman |
| 4,281,373 A | 7/1981 | Mabille |
| 4,287,557 A | 9/1981 | Brehse |
| 4,303,073 A | 12/1981 | Archibald |
| 4,304,235 A | 12/1981 | Kaufman |
| 4,311,154 A | 1/1982 | Sterzer et al. |
| 4,314,559 A | 2/1982 | Allen |
| 4,321,926 A | 3/1982 | Roge |
| 4,331,149 A | 5/1982 | Gonser |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,381,789 A | 5/1983 | Naser et al. |
| 4,384,582 A | 5/1983 | Watt |
| 4,387,714 A | 6/1983 | Geddes et al. |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,437,464 A | 3/1984 | Crow |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Paterson |
| 4,643,193 A | 2/1987 | DeMarzo |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,369 A | 5/1987 | Ensslin |
| 4,662,383 A | 5/1987 | Sogawa et al. |
| 4,669,468 A | 6/1987 | Cartmell et al. |
| 4,699,146 A | 10/1987 | Sieverding |
| 4,712,559 A | 12/1987 | Turner |
| 4,722,761 A | 2/1988 | Cartmell et al. |
| 4,725,713 A | 2/1988 | Lehrke |
| 4,727,874 A | 3/1988 | Bowers et al. |
| 4,735,204 A | 4/1988 | Sussman et al. |

(56) References Cited

U.S. PATENT DOCUMENTS

| | | |
|---|---|---|
| 4,739,759 A | 4/1988 | Rexroth et al. |
| 4,741,334 A | 5/1988 | Irnich |
| 4,745,918 A | 5/1988 | Feucht |
| 4,748,983 A | 6/1988 | Shigeta et al. |
| 4,750,482 A | 6/1988 | Sieverding |
| 4,754,757 A | 7/1988 | Feucht |
| 4,768,514 A | 9/1988 | DeMarzo |
| 4,770,173 A | 9/1988 | Feucht et al. |
| 4,788,977 A | 12/1988 | Farin et al. |
| 4,799,480 A | 1/1989 | Abraham et al. |
| 4,805,621 A | 2/1989 | Heinze et al. |
| 4,807,621 A | 2/1989 | Hagen et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,844,063 A | 7/1989 | Clark |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |
| 4,873,974 A | 10/1989 | Hagen et al. |
| 4,880,719 A | 11/1989 | Murofushi et al. |
| 4,890,610 A | 1/1990 | Kirwan et al. |
| 4,895,169 A | 1/1990 | Heath |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,947,846 A | 8/1990 | Kitagawa et al. |
| 4,955,381 A | 9/1990 | Way et al. |
| 4,961,047 A | 10/1990 | Carder |
| 4,961,435 A | 10/1990 | Kitagawa et al. |
| 4,966,597 A | 10/1990 | Cosman |
| RE33,420 E | 11/1990 | Sussman |
| 4,969,885 A | 11/1990 | Farin |
| 4,993,430 A | 2/1991 | Shimoyama et al. |
| 4,995,877 A | 2/1991 | Ams et al. |
| 5,000,753 A | 3/1991 | Hagen et al. |
| 5,004,425 A | 4/1991 | Hee |
| 5,010,896 A | 4/1991 | Westbrook |
| 5,015,227 A | 5/1991 | Broadwin et al. |
| 5,019,176 A | 5/1991 | Brandhorst, Jr. |
| 5,029,588 A | 7/1991 | Yock et al. |
| 5,042,981 A | 8/1991 | Gross |
| 5,087,257 A | 2/1992 | Farin |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,162,217 A | 11/1992 | Hartman |
| 5,167,658 A | 12/1992 | Ensslin |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,246,439 A | 9/1993 | Hebborn et al. |
| 5,249,585 A | 10/1993 | Turner et al. |
| 5,267,994 A | 12/1993 | Gentelia et al. |
| 5,267,997 A | 12/1993 | Farin |
| 5,271,417 A | 12/1993 | Swanson et al. |
| 5,276,079 A | 1/1994 | Duan et al. |
| 5,281,213 A | 1/1994 | Milder et al. |
| 5,286,255 A | 2/1994 | Weber |
| 5,300,068 A | 4/1994 | Rosar et al. |
| 5,300,070 A | 4/1994 | Gentelia et al. |
| 5,312,401 A | 5/1994 | Newton et al. |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,193 A | 8/1994 | Nardella |
| 5,336,255 A | 8/1994 | Kanare et al. |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,348,554 A | 9/1994 | Imran et al. |
| 5,362,420 A | 11/1994 | Itoh et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,385,679 A | 1/1995 | Uy et al. |
| 5,388,490 A | 2/1995 | Buck |
| 5,389,376 A | 2/1995 | Duan et al. |
| 5,390,382 A | 2/1995 | Hannant et al. |
| 5,396,062 A | 3/1995 | Eisentraut et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,006 A | 4/1995 | Buchholtz et al. |
| 5,409,485 A | 4/1995 | Suda |
| 5,409,966 A | 4/1995 | Duan et al. |
| 5,413,573 A | 5/1995 | Koivukangas |
| 5,417,719 A | 5/1995 | Hull et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,430,434 A | 7/1995 | Lederer et al. |
| 5,432,459 A | 7/1995 | Thompson |
| 5,433,739 A | 7/1995 | Sluijter et al. |
| 5,434,398 A | 7/1995 | Goldberg |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,447,513 A | 9/1995 | Davison et al. |
| 5,449,365 A | 9/1995 | Green et al. |
| 5,451,224 A | 9/1995 | Goble et al. |
| 5,452,725 A | 9/1995 | Martenson |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,478,303 A | 12/1995 | Folry-Nolan et al. |
| 5,480,399 A | 1/1996 | Hebborn |
| 5,483,952 A | 1/1996 | Aranyi |
| 5,490,850 A | 2/1996 | Ellman et al. |
| 5,496,312 A | 3/1996 | Klicek |
| 5,496,313 A | 3/1996 | Gentelia et al. |
| 5,496,363 A | 3/1996 | Burgio et al. |
| 5,500,012 A | 3/1996 | Brucker et al. |
| 5,500,616 A | 3/1996 | Ochi |
| 5,514,129 A | 5/1996 | Smith |
| 5,520,180 A | 5/1996 | Uy et al. |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,536,446 A | 7/1996 | Uy et al. |
| 5,540,681 A | 7/1996 | Strul et al. |
| 5,540,683 A | 7/1996 | Ichikawa |
| 5,540,684 A | 7/1996 | Hassler, Jr. |
| 5,540,724 A | 7/1996 | Cox |
| 5,556,396 A | 9/1996 | Cohen et al. |
| 5,558,671 A | 9/1996 | Yates |

(56) References Cited

U.S. PATENT DOCUMENTS

| | | |
|---|---|---|
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,594,636 A | 1/1997 | Schauder |
| 5,596,466 A | 1/1997 | Ochi |
| 5,599,344 A | 2/1997 | Paterson |
| 5,599,345 A | 2/1997 | Edwards et al. |
| 5,601,618 A | 2/1997 | James |
| 5,605,150 A | 2/1997 | Radons et al. |
| 5,611,709 A | 3/1997 | McAnulty |
| 5,613,966 A | 3/1997 | Makower et al. |
| 5,613,996 A | 3/1997 | Lindsay |
| 5,625,370 A | 4/1997 | D'Hont |
| 5,626,575 A | 5/1997 | Crenner |
| 5,628,745 A | 5/1997 | Bek |
| 5,632,280 A | 5/1997 | Leyde et al. |
| 5,643,319 A | 7/1997 | Green et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,660,892 A | 8/1997 | Robbins et al. |
| 5,663,899 A | 9/1997 | Zvonar et al. |
| 5,670,557 A | 9/1997 | Dietz et al. |
| 5,674,561 A | 10/1997 | Dietz et al. |
| 5,678,545 A | 10/1997 | Stratbucker |
| 5,688,267 A | 11/1997 | Panescu et al. |
| 5,688,269 A | 11/1997 | Newton et al. |
| 5,690,692 A | 11/1997 | Fleming |
| 5,693,042 A | 12/1997 | Boiarski et al. |
| 5,695,494 A | 12/1997 | Becker |
| 5,696,351 A | 12/1997 | Benn et al. |
| 5,702,386 A | 12/1997 | Stern et al. |
| 5,702,429 A | 12/1997 | King |
| 5,707,369 A | 1/1998 | Vaitekunas et al. |
| 5,713,896 A | 2/1998 | Nardella |
| 5,720,744 A | 2/1998 | Eggleston et al. |
| 5,722,975 A | 3/1998 | Edwards et al. |
| 5,733,281 A | 3/1998 | Nardella |
| 5,749,869 A | 5/1998 | Lindenmeier et al. |
| 5,749,871 A | 5/1998 | Hood et al. |
| 5,755,715 A | 5/1998 | Stern |
| 5,766,165 A | 6/1998 | Gentelia et al. |
| 5,769,847 A | 6/1998 | Panescu |
| 5,772,659 A | 6/1998 | Becker et al. |
| 5,779,632 A | 7/1998 | Dietz et al. |
| 5,792,138 A | 8/1998 | Shipp |
| 5,797,802 A | 8/1998 | Nowak |
| 5,797,902 A | 8/1998 | Netherly |
| 5,800,426 A | 9/1998 | Taki et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,836,942 A | 11/1998 | Netherly et al. |
| 5,836,943 A | 11/1998 | Miller, III |
| 5,836,990 A | 11/1998 | Li |
| 5,846,236 A | 12/1998 | Lindenmeier et al. |
| 5,846,558 A | 12/1998 | Nielsen et al. |
| 5,853,750 A | 12/1998 | Dietz et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,868,742 A | 2/1999 | Manes et al. |
| 5,871,481 A | 2/1999 | Kannenberg et al. |
| 5,897,552 A | 4/1999 | Edwards et al. |
| 5,908,444 A | 6/1999 | Azure |
| 5,913,882 A | 6/1999 | King |
| 5,921,982 A | 7/1999 | Lesh et al. |
| 5,924,983 A | 7/1999 | Takaki et al. |
| 5,925,070 A | 7/1999 | King et al. |
| 5,931,836 A | 8/1999 | Hatta et al. |
| 5,938,690 A | 8/1999 | Law et al. |
| 5,947,961 A | 9/1999 | Netherly |
| 5,948,007 A | 9/1999 | Starkenbaum et al. |
| 5,951,545 A | 9/1999 | Schilling |
| 5,951,546 A | 9/1999 | Lorentzen |
| 5,952,398 A | 9/1999 | Dietz et al. |
| 5,954,686 A | 9/1999 | Garito et al. |
| 5,954,717 A | 9/1999 | Behl et al. |
| 5,961,344 A | 10/1999 | Rosales et al. |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,985,990 A | 11/1999 | Kantner et al. |
| 5,999,061 A | 12/1999 | Pope et al. |
| 6,007,532 A | 12/1999 | Netherly |
| 6,010,054 A | 1/2000 | Johnson et al. |
| 6,010,499 A | 1/2000 | Cobb |
| 6,014,581 A | 1/2000 | Whayne et al. |
| 6,030,381 A | 2/2000 | Jones et al. |
| 6,032,063 A | 2/2000 | Hoar et al. |
| 6,033,399 A | 3/2000 | Gines |
| 6,039,732 A | 3/2000 | Ichikawa et al. |
| 6,044,283 A | 3/2000 | Fein et al. |
| 6,053,910 A | 4/2000 | Fleenor |
| 6,053,912 A | 4/2000 | Panescu et al. |
| RE36,720 E | 5/2000 | Green et al. |
| 6,056,745 A | 5/2000 | Panescu et al. |
| 6,056,746 A | 5/2000 | Goble et al. |
| 6,059,778 A | 5/2000 | Sherman |
| 6,063,075 A | 5/2000 | Mihori |
| 6,063,078 A | 5/2000 | Wittkampf |
| 6,068,627 A | 5/2000 | Orszulak et al. |
| 6,074,386 A | 6/2000 | Goble et al. |
| 6,080,149 A | 6/2000 | Huang et al. |
| 6,083,221 A | 7/2000 | Fleenor et al. |
| 6,086,249 A | 7/2000 | Urich |
| 6,093,186 A | 7/2000 | Goble |
| RE36,871 E | 9/2000 | Epstein |
| 6,113,591 A | 9/2000 | Whayne et al. |
| 6,113,596 A | 9/2000 | Hooven |
| 6,121,508 A | 9/2000 | Bischof et al. |
| 6,123,702 A | 9/2000 | Swanson et al. |
| 6,132,429 A | 10/2000 | Baker |
| 6,135,953 A | 10/2000 | Carim |
| 6,142,992 A | 11/2000 | Cheng et al. |
| 6,162,217 A | 12/2000 | Kannenberg et al. |
| 6,171,304 B1 | 1/2001 | Netherly et al. |
| 6,200,314 B1 | 3/2001 | Sherman |
| 6,203,541 B1 | 3/2001 | Keppel |
| 6,210,403 B1 | 4/2001 | Klicek |
| 6,214,000 B1 | 4/2001 | Fleenor et al. |
| 6,228,080 B1 | 5/2001 | Gines |
| 6,228,081 B1 | 5/2001 | Goble |
| 6,231,569 B1 | 5/2001 | Bek |
| 6,232,366 B1 | 5/2001 | Wang et al. |
| 6,235,020 B1 | 5/2001 | Cheng et al. |
| 6,238,387 B1 | 5/2001 | Miller, III |
| 6,238,388 B1 | 5/2001 | Ellman |
| 6,240,323 B1 | 5/2001 | Calenzo, Sr. et al. |
| 6,241,725 B1 | 6/2001 | Cosman |
| 6,245,065 B1 | 6/2001 | Panescu |
| 6,246,912 B1 | 6/2001 | Sluijter et al. |
| 6,251,106 B1 | 6/2001 | Becker et al. |
| 6,258,085 B1 | 7/2001 | Eggleston |
| 6,261,285 B1 | 7/2001 | Novak |
| 6,261,286 B1 | 7/2001 | Goble et al. |
| 6,273,886 B1 | 8/2001 | Edwards et al. |
| 6,275,786 B1 | 8/2001 | Daners |
| 6,293,941 B1 | 9/2001 | Strul |
| 6,293,942 B1 | 9/2001 | Goble et al. |
| 6,301,500 B1 | 10/2001 | Van Herk et al. |
| 6,306,131 B1 | 10/2001 | Hareyama et al. |
| 6,306,134 B1 | 10/2001 | Goble et al. |
| 6,309,386 B1 | 10/2001 | Bek |
| 6,310,611 B1 | 10/2001 | Caldwell |

(56) References Cited

U.S. PATENT DOCUMENTS

| | | |
|---|---|---|
| 6,337,998 B1 | 1/2002 | Behl et al. |
| 6,338,657 B1 | 1/2002 | Harper et al. |
| 6,347,246 B1 | 2/2002 | Perrault et al. |
| 6,350,264 B1 | 2/2002 | Hooven |
| 6,357,089 B1 | 3/2002 | Koguchi et al. |
| 6,358,245 B1 | 3/2002 | Edwards et al. |
| 6,364,877 B1 | 4/2002 | Goble et al. |
| 6,379,161 B1 | 4/2002 | Ma |
| 6,383,183 B1 | 5/2002 | Sekino et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,743 B1 | 6/2002 | Orszulak et al. |
| 6,409,722 B1 | 6/2002 | Hoey et al. |
| 6,415,170 B1 | 7/2002 | Loutis et al. |
| 6,416,509 B1 | 7/2002 | Goble et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,764 B1 | 9/2002 | Fleenor et al. |
| 6,458,121 B1 | 10/2002 | Rosenstock |
| 6,464,689 B1 | 10/2002 | Qin |
| 6,464,696 B1 | 10/2002 | Oyama |
| 6,488,678 B2 | 12/2002 | Sherman |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside et al. |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,547,786 B1 | 4/2003 | Goble |
| 6,558,376 B2 | 5/2003 | Bishop |
| 6,562,037 B2 | 5/2003 | Paton |
| 6,565,559 B2 | 5/2003 | Eggleston |
| 6,569,160 B1 | 5/2003 | Goldin et al. |
| 6,573,248 B2 | 6/2003 | Ramasamy et al. |
| 6,575,969 B1 | 6/2003 | Rittman, III et al. |
| 6,582,424 B2 | 6/2003 | Fleenor et al. |
| 6,582,427 B1 | 6/2003 | Goble et al. |
| 6,602,243 B2 | 8/2003 | Noda |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,635,057 B2 | 10/2003 | Harano |
| 6,648,883 B2 | 11/2003 | Francischelli |
| 6,652,514 B2 | 11/2003 | Ellman |
| 6,663,623 B1 | 12/2003 | Oyama et al. |
| 6,663,624 B2 | 12/2003 | Edwards |
| 6,666,859 B1 | 12/2003 | Fleenor et al. |
| 6,666,860 B1 | 12/2003 | Takahashi |
| 6,669,073 B2 | 12/2003 | Milliman et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,692,489 B1 | 2/2004 | Heim |
| 6,712,813 B2 | 3/2004 | Ellman |
| 6,730,080 B2 | 5/2004 | Harano |
| 6,733,495 B1 | 5/2004 | Bek |
| 6,733,498 B2 | 5/2004 | Paton |
| 6,736,810 B2 * | 5/2004 | Hoey et al. ............... 606/34 |
| 6,740,079 B1 | 5/2004 | Eggers |
| 6,740,085 B2 | 5/2004 | Hareyama |
| 6,783,523 B2 | 8/2004 | Qin |
| 6,790,206 B2 | 9/2004 | Panescu |
| 6,796,828 B2 | 9/2004 | Ehr et al. |
| 6,796,981 B2 | 9/2004 | Wham |
| 6,799,063 B2 | 9/2004 | Carson |
| 6,824,539 B2 | 11/2004 | Novak |
| 6,830,569 B2 | 12/2004 | Thompson |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,892,086 B2 | 5/2005 | Russell |
| 6,893,435 B2 | 5/2005 | Goble |
| 6,939,344 B2 | 9/2005 | Kreindel |
| 6,948,503 B2 | 9/2005 | Refior et al. |
| 6,953,139 B2 | 10/2005 | Milliman et al. |
| 6,959,852 B2 | 11/2005 | Shelton, IV et al. |
| 6,997,735 B2 | 2/2006 | Ehr et al. |
| 7,128,253 B2 | 10/2006 | Mastri et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 2001/0014804 A1 | 8/2001 | Goble et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0058933 A1* | 5/2002 | Christopherson et al. ...... 606/34 |
| 2002/0068932 A1 | 6/2002 | Edwards |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0199863 A1 | 10/2003 | Swanson |
| 2004/0002745 A1 | 1/2004 | Flemming |
| 2004/0015163 A1 | 1/2004 | Buysse et al. |
| 2004/0019347 A1 | 1/2004 | Sakurai |
| 2004/0024395 A1 | 2/2004 | Ellman |
| 2004/0030328 A1 | 2/2004 | Eggers |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0021020 A1 | 1/2005 | Blaha et al. |
| 2005/0021022 A1 | 1/2005 | Sturm et al. |
| 2005/0079752 A1 | 4/2005 | Ehr et al. |
| 2005/0085806 A1 | 4/2005 | Auge, II et al. |
| 2005/0101947 A1 | 5/2005 | Jarrard et al. |
| 2005/0101951 A1 | 5/2005 | Wham |
| 2005/0109111 A1 | 5/2005 | Manlove et al. |
| 2005/0113818 A1 | 5/2005 | Sartor |
| 2005/0113819 A1 | 5/2005 | Wham |
| 2005/0149151 A1 | 7/2005 | Orszulak |

(56) References Cited

U.S. PATENT DOCUMENTS

| | | |
|---|---|---|
| 2005/0182398 A1 | 8/2005 | Paterson |
| 2005/0197659 A1 | 9/2005 | Bahney |
| 2005/0203504 A1 | 9/2005 | Wham et al. |
| 2005/0251130 A1 | 11/2005 | Boveja et al. |
| 2006/0025760 A1 | 2/2006 | Podhajsky |
| 2006/0030195 A1 | 2/2006 | Ehr et al. |
| 2006/0041251 A1 | 2/2006 | Odell et al. |
| 2006/0041252 A1 | 2/2006 | Odell et al. |
| 2006/0041253 A1 | 2/2006 | Newton et al. |
| 2006/0074411 A1 | 4/2006 | Carmel et al. |
| 2006/0079872 A1 | 4/2006 | Eggleston |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 | 3/2007 | Eggleston |
| 2007/0049916 A1 | 3/2007 | Isaacson et al. |
| 2007/0049919 A1 | 3/2007 | Lee, Jr. et al. |
| 2007/0073284 A1 | 3/2007 | Sturm |
| 2007/0074719 A1 | 4/2007 | Danek et al. |
| 2007/0161979 A1 | 7/2007 | McPherson |
| 2007/0167942 A1 | 7/2007 | Rick |
| 2007/0203481 A1 | 8/2007 | Gregg et al. |
| 2007/0225698 A1 | 9/2007 | Orszulak et al. |
| 2007/0244478 A1 | 10/2007 | Bahney |
| 2008/0009846 A1 | 1/2008 | Ward |
| 2008/0033276 A1 | 2/2008 | Ehr et al. |
| 2008/0083806 A1 | 4/2008 | Scirica |
| 2008/0083813 A1 | 4/2008 | Zemlok et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 42 38 263 A1 | 5/1993 |
| DE | 4339049 | 5/1995 |
| DE | 197 17 411 A1 | 11/1998 |
| DE | 19717411 | 11/1998 |
| DE | 198 01 173 | 7/1999 |
| DE | 19848540 | 5/2000 |
| DE | 103 28 514 | 6/2003 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 878169 | 11/1998 |
| EP | 0 930 048 | 7/1999 |
| EP | 1 051 949 A1 | 11/2000 |
| EP | 1051948 | 11/2000 |
| EP | 1293171 | 3/2003 |
| EP | 1 468 653 | 10/2004 |
| EP | 1 645 236 | 4/2006 |
| EP | 880220 | 6/2006 |
| EP | 1 808 144 | 7/2007 |
| FR | 1275415 | 10/1961 |
| FR | 1347865 | 11/1963 |
| FR | 2276027 | 6/1974 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2 054 382 | 2/1981 |
| GB | 2164473 | 3/1986 |
| GB | 2214430 | 9/1989 |
| GB | 2358934 | 8/2001 |
| JP | 04242092 | 8/1992 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO02/11634 | 2/2002 |
| WO | WO02/45589 | 6/2002 |
| WO | WO02/47565 | 6/2002 |
| WO | WO02/088128 | 7/2002 |
| WO | WO 02/058579 | 8/2002 |
| WO | WO 02/060526 | 8/2002 |
| WO | WO 02/099442 | 12/2002 |
| WO | WO03/092520 | 11/2003 |
| WO | WO 03/094766 | 11/2003 |
| WO | WO2005/060365 | 11/2003 |
| WO | WO 2004/028385 | 4/2004 |
| WO | WO2004/028385 | 4/2004 |
| WO | WO2004/098385 | 4/2004 |
| WO | WO 2004/074854 | 9/2004 |
| WO | WO2005/046496 | 5/2005 |
| WO | WO 2005/048809 | 6/2005 |
| WO | WO2005/048809 | 6/2005 |
| WO | WO2005/050151 | 6/2005 |
| WO | WO 2005/087124 | 9/2005 |
| WO | WO 2005/110263 | 11/2005 |

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

(56) References Cited

OTHER PUBLICATIONS

Astrahan, "A Localized Current Field Hyperthermia System for Use with 192-Iridium Interstitial Implants" Medical Physics, 9 (3), May/Jun. 1982.
Bergdahl et al. "Studies on Coagulation and the Development of an Automatic Computerized Bipolar Coagulator" J. Neurosurg, vol. 75, Jul. 1991, pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In Wiliam RH, Rengachary SS (eds): Neurosurgery, New York; McGraw-Hill, vol. 111, (1984), pp. 2490-2499.
Cosman et al. "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation—'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report from EP 06006961 dated Aug. 3, 2006.
Medtrex Brochure—Total Control at Full Speed, "The O.R. Pro 300" 1 p. Sep. 1998.
International Search Report EP04707738 dated Jul. 4, 2007.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Muller et al. "Extended Left Hemicolectomy Using the LigaSure Vessel Sealing System" Innovations That Work; Company Newsletter; Sep. 1999.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(2005-03); pp. 160-164.
Bergdahl et al., "Studies on Coagulation and the Development of an Automatic Computerized Bipolar Coagulator" Journal of Neurosurgery 75:1, (Jul. 1991) pp. 148-151.
International Search Report EP 05021944.3 dated Jan. 25, 2006.
International Search Report EP 05002027.0 dated May 12, 2005.
Official Action issued by Australian Patent Office in counterpart Australian Patent Application No. 2003284929 mailed Sep. 9, 2009.
International Search Report PCT/US2004/004196 dated Oct. 4, 2007.
International Search Report EP06006961.4 dated Oct. 5, 2007.
International Search Report EP07000885.9 dated May 2, 2007.
International Search Report EP07007783.9 dated Aug. 6, 2007.
International Search Report EP06018206.0 dated Oct. 13, 2006.
European Search Report issued by European Patent Office in counterpart European Patent Application No. 10179321.4 mailed Mar. 18, 2011.

* cited by examiner

REDUNDANT TEMPERATURE MONITORING IN ELECTROSURGICAL SYSTEMS FOR SAFETY MITIGATION

BACKGROUND

1. Technical Field

The present invention is directed to electrosurgical systems, and, in particular, to a redundant temperature monitoring system and method for an electrosurgical system for safety mitigation.

2. Description of the Related Art

Electrosurgical generators are employed by surgeons in conjunction with an electrosurgical tool to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical generators typically include power supply circuits, front panel interface circuits, and RF output stage circuits. Many electrical designs for electrosurgical generators are known in the field. In certain electrosurgical generator designs, the RF output stage can be adjusted to control the RMS (root mean square) output power. The methods of controlling the RF output stage may include changing the duty cycle, or changing the amplitude of the driving signal to the RF output stage. The method of controlling the RF output stage is described herein as changing an input to the RF output stage.

Electrosurgical techniques have been used to seal or fuse small diameter blood vessels, vascular bundles and tissue. In this application, two layers of tissue are grasped and clamped together while electrosurgical power is applied. By applying a unique combination of pressure, gap distance between opposing seal surfaces and controlling the electrosurgical energy, the two tissue layers are welded or fused together into a single mass with limited demarcation between tissue layers. Tissue fusion is similar to vessel sealing, except that a vessel or duct is not necessarily sealed in this process. For example, tissue fusion may be used instead of staples for surgical anastomosis. Electrosurgical power has a desiccating effect on tissue during tissue fusion or vessel sealing.

One of the issues associated with electrosurgical sealing or fusion of tissue is undesirable collateral damage to tissue due to the various thermal effects associated with electrosurgically energizing tissue. The tissue at the operative site is heated by electrosurgical current typically applied by the electrosurgical instrument. Healthy tissue adjacent to the operative site may become thermally damaged if too much heat is allowed to build up at the operative site or adjacent the sealing surfaces. For example, during sealing, the heat may conduct or spread to the adjacent tissue and cause a significant region of tissue necrosis. This is known as thermal spread. Thermal spread becomes important when electrosurgical instruments are used in close proximity to delicate anatomical structures. Therefore, an electrosurgical generator that reduced the possibility of thermal spread would offer a better opportunity for a successful surgical outcome.

Another issue associated with electrosurgical tissue sealing or tissue fusion is the buildup of eschar on the surgical instrument. Eschar is a deposit which is created from tissue that is charred by heat. Surgical tools often lose effectiveness when coated with eschar.

Conventional electrosurgical systems have employed temperature sensors in the surgical tool to monitor conditions at the operative site and/or the temperature of the tissue being manipulated. An exemplary temperature sensor used in such systems is a thermocouple due to its small size and low cost. However, thermocouples require compensation circuitry to achieve a desired level of accuracy, which increases the complexity of the temperature monitoring circuit and introduces additional possible points of failure. For example, if a compensation circuit fails, the electrosurgical system will still read a temperature, although possibly wrong. A technician or physician may increase output power believing they have not reached a critical temperature while actually applying too much power to the operative site causing damage to tissues and surrounding anatomical structures.

Therefore, it would be desirable to have a temperature monitoring circuit for an electrosurgical system for accurately determining a temperature of an operative site and/or tissue of a patient. Furthermore, it would be desirable to have a temperature monitoring circuit for controlling an electrosurgical generator for producing a clinically effective output and, in addition, for detecting failures of the temperature measurement circuit.

SUMMARY

A redundant temperature monitoring system and method for an electrosurgical system are provided.

According to an aspect of the present disclosure, a temperature monitoring circuit includes at least one temperature sensor for sensing a temperature at a measuring point, a first temperature measurement circuit coupled to the at least one temperature sensor for generating a first temperature value, a second temperature measurement circuit coupled to the at least one temperature sensor for generating a second temperature value, and a control circuit for determining a difference between the first and second temperature values and for comparing the difference to a first predetermined threshold. If the difference is greater than the first predetermined threshold, the control circuit generates a warning signal. If the difference is greater than a second predetermined threshold, the control circuit generates an alarm signal and/or shuts down a power source.

According to another embodiment of the present disclosure, an electrosurgical generator is provided comprising a radio frequency (RF) output circuit for outputting RF energy; a control circuit for controlling the output of the RF output circuit; and a temperature monitoring circuit comprising at least one temperature sensor for sensing a temperature at a measuring point, a first temperature measurement circuit coupled to the at least one temperature sensor for generating a first temperature value, a second temperature measurement circuit coupled to the at least one temperature sensor for generating a second temperature value, and a control circuit for determining a difference between the first and second temperature values and for comparing the difference to a first predetermined threshold. If the difference is greater than the first predetermined threshold, the control circuit generates a warning signal and, if the difference is greater than the second predetermined threshold, the control circuit generates an alarm signal.

Preferably, the electrosurgical generator further comprises a display for displaying the warning and/or alarm signal. Furthermore, the electrosurgical generator may comprise an audio output for audibly producing the warning and/or alarm signal.

According to yet another embodiment of the present disclosure, an electrosurgical system includes an electrosurgical generator for outputting radio frequency (RF) energy; an electrosurgical instrument coupled to the electrosurgical generator for applying the RF energy to an operative site; and a temperature monitoring circuit comprising at least one temperature sensor for sensing a temperature at a measuring point, a first temperature measurement circuit coupled to the at least one temperature sensor for generating a first temperature value, a second temperature measurement circuit coupled to the at least one temperature sensor for generating a second temperature value, and a control circuit for determining a difference between the first and second temperature values and for comparing the difference to a first predetermined threshold. Furthermore, the electrosurgical instrument includes as least one end effector member and the at least one temperature sensor is located in the at least one end effector member.

In a further aspect of the present invention, a method for controlling an electrosurgical system is provided. The method comprises the steps of reading a first temperature value at an operative site; reading a second temperature value at the operative site; determining a difference of the first and second temperature values; determining if the difference is greater than a first predetermined threshold, wherein when the difference is greater than the first predetermined threshold, generating a warning signal. The method further comprises the step of, wherein when the difference is greater than a second predetermined threshold, generating an alarm signal. Additionally, the method comprises the step of shutting down the electrosurgical system when the difference is greater than a second predetermined threshold.

BRIEF DESCRIPTION OF THE DRAWINGS

The above and other aspects, features, and advantages of the present invention will become more apparent in light of the following detailed description when taken in conjunction with the accompanying drawings in which.

DETAILED DESCRIPTION

Figure 1:
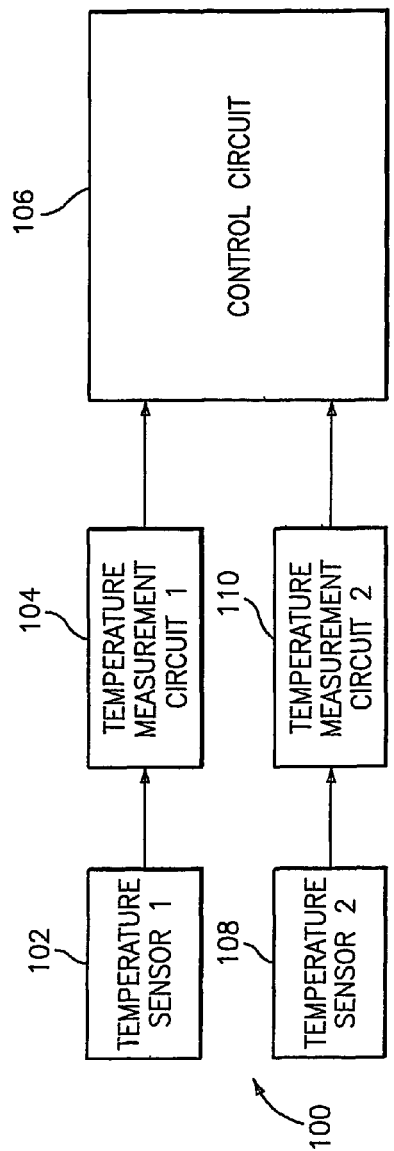
FIG. 1 is a block diagram of a redundant temperature monitoring system according to an embodiment of the present invention.

Embodiments of the present invention will be described herein below with reference to the accompanying drawings. In the following description, well-known functions or constructions are not described in detail to avoid obscuring the invention in unnecessary detail. In the figures, like reference numerals represent like elements.

A redundant temperature monitoring system and method for an electrosurgical system are provided. Redundant temperature monitoring for medical devices using temperature as a control parameter will provide a safety mitiagtor should one of the monitoring or measurement circuits fail or malfunction. Redundant measurement circuits will read temperatures at a measuring point and lead the temperatures into a control circuit for controlling the electrosurgical system. If the values read from the redundant measurement circuit diverge from one another by more than a specified amount, the control circuit or device will recognize a discrepancy and take the appropriate course of action, e.g., alarm, warn, shutdown.

Referring to FIG. 1, a redundant temperature monitoring system 100 according to an embodiment of the present invention is provided. The system 100 includes a first temperature sensor 102, a first temperature measurement circuit 104, a second temperature sensor 108, a second temperature measurement circuit 110 and a control circuit 106. The first temperature sensor 102 is electrically coupled to the first temperature measurement circuit 104 and will send a first electrical signal indicative of a temperature sensed at a measuring point to the control circuit 106. Likewise, the second temperature sensor 108 is electrically coupled to the second temperature measurement circuit 110 and will send a second electrical signal indicative of a temperature sensed at the measuring point to the control circuit 106. The control circuit 106 will determine a difference between the first and second temperatures sensed. Additionally, the control circuit will compare the difference to a plurality of thresholds and will initiate an appropriate action depending on the magnitude of the difference.

The first and second temperature sensors 102, 108 may be any known temperature sensor in the art, for example, a thermocouple, thermistor, resistance temperature detector (RTD), semiconductor thermometer device, etc. It is to be appreciated that the temperature measurement circuit 104, 110 will be matched to the type of temperature sensor being employed.

Figure 2:
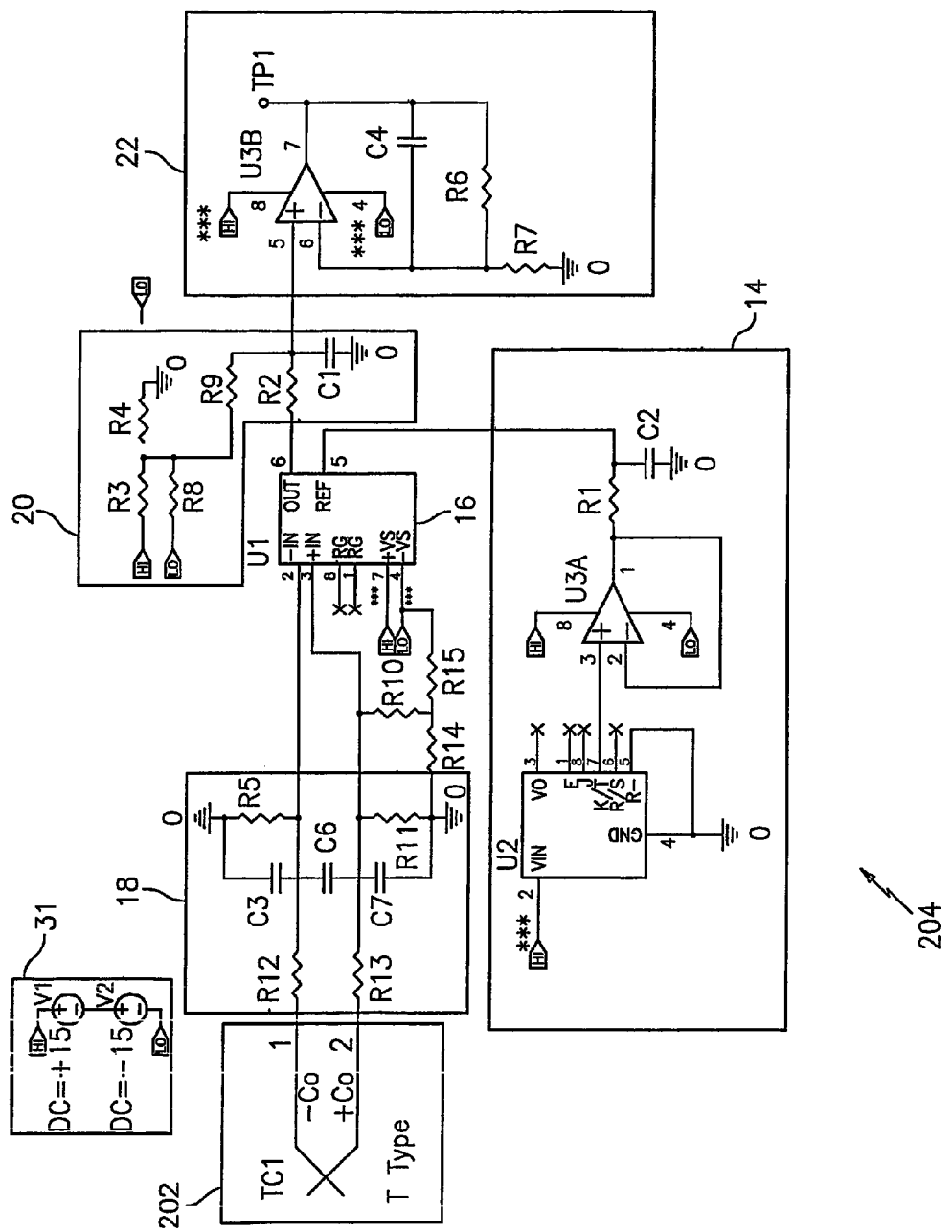
FIG. 2 is a schematic diagram of an exemplary thermocouple measurement circuit in accordance with the present invention.

Referring to FIG. 2, an exemplary temperature sensor 202 and temperature measurement circuit 204 is shown. The temperature measurement circuit shown in FIG. 2 is described in U.S. patent application Ser. No. 10/573,314, entitled "THERMOCOUPLE MEASUREMENT CIRICUT," by Derek M. Blaha, filed herewith, now U.S. Pat. No. 8,104,956, which is incorporated by reference herein in its entirety and assigned to the common assignee of the present invention. The thermocouple measurement circuit 204 generally includes a thermocouple input 202 for sensing a temperature of a measuring point, a compensation circuit 14 for compensating thermocouple effects of junctions of the hermocouple 202 and an instrumentation amplifier 16 for summing an output of the thermocouple and an output of the compensation circuit and outputting a voltage indicative of the temperature sensed. The thermocouple measurement circuit 204 may also include a filtering circuit 18 for eliminating noise from the thermocouple input 202 and an offset 20 and gain 22 circuit for scaling an output of the thermocouple measurement circuit 204. A power supply circuit 31 is employed to provide a high voltage output, e.g., +15 VDC, and a low voltage output, e.g., −15 VDC, for energizing any component requiring power in the thermocouple measurement circuit 204. Optionally, the thermocouple measurement circuit 204 may Include analog-to-digital converter for converting the analog output voltage to a digital signal.

As a further example, if a resistance temperature device (RTD) is employed as the temperature sensor, the temperature measurement circuit will include a current source to pass current through the RTD and a voltage reading means to read the voltage-drop produced across the RTD. From the current and voltage, a resistance value can be derived which is indicative of the temperature being sensed.

The control circuit 106 receives the electrical signal indicative of a temperature sensed from each of the first and second temperature measurement circuits 104, 110. The control circuit determines a difference between the temperature values received from the first and second temperature measurement circuit. The control circuit compares the difference to a plurality of threshold to determine if the temperature measurement circuits 104, 110 are operating correctly. The control circuit 106 may be a hardwired device such as a field-programmable gate array (FPGA) or programmable logic device (PLD), or a microprocessor including necessary software modules to perform the above described functions. Upon a result of the comparison, the control circuit 106 may generate a warning or alarm signal and/or may initiate routines to control an output of a heat generating device or power source.

Figure 3:
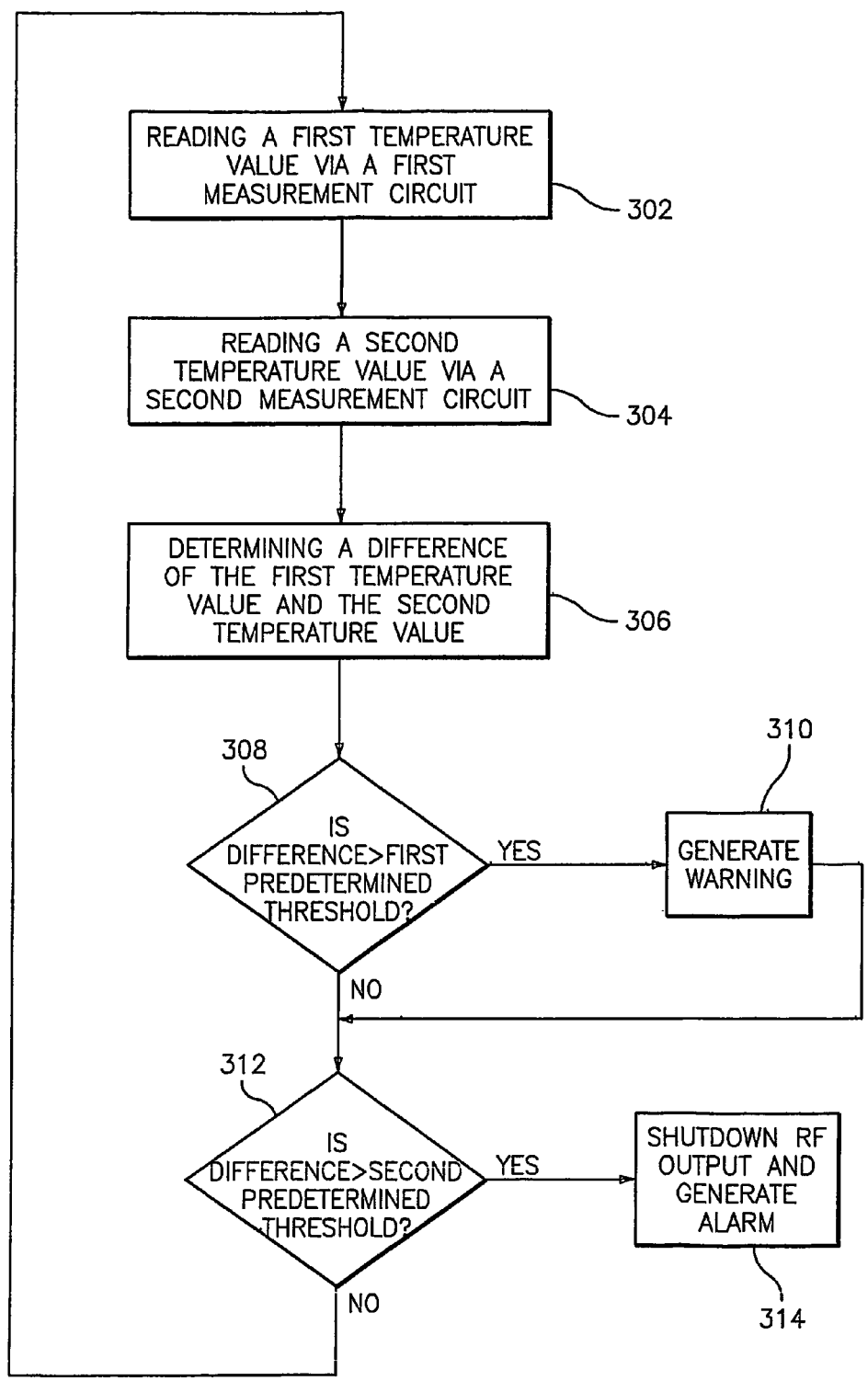
FIG. 3 is a flowchart illustrating a method for monitoring temperature in an electrosurgical generator according to an embodiment of the present invention.

An operation of the redundant temperature monitoring system will now be described with reference to FIG. 3. In step 302, a first temperature value is read by the first temperature sensor 102 and sent to the control circuit 106 via the first temperature measurement circuit 104. In step 304, a second temperature value is read by the second temperature sensor 108 and sent to the control circuit 106 via the second temperature measurement circuit 110. In step 306, the control circuit 106 determines a difference between the first and second temperature values.

The temperature difference is then compared to a plurality of thresholds. In step 308, the temperature difference is compared to a first predetermined threshold. The first predetermined threshold represents a minimum allowable deviation of the measured temperatures. If the temperature difference is greater than the first predetermined threshold, the control circuit 106 generates a warning to a user of the system indicating there may be a problem with one of the temperature measuring circuits 104, 110 (step 310) and then continues to monitor the first and second temperature values. If the temperature difference is less than the first predetermined threshold, the system continues to monitor the temperature at the measuring point.

Furthermore, the control circuit 106 compares the temperature difference to a second predetermined threshold (step 312). The second predetermined threshold is a maximum allowable deviation of the measured temperatures. If the temperature difference is greater than the second predetermined threshold, the control circuit 106 generates an alarm to the user indicating that there is a problem with the temperature measurement circuits 104, 110 (step 314). Additionally, the control circuit 106 may shut down or take control of a source of the heat generation, e.g., a power source.

Figure 4:
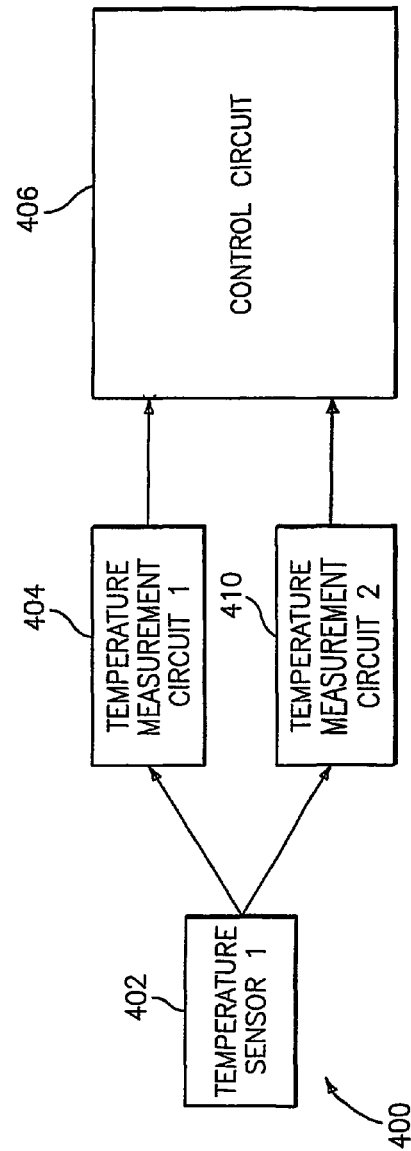
FIG. 4 is a block diagram of a redundant temperature monitoring system according to another embodiment of the present invention.

It is to be appreciated that the redundant temperature monitoring system of the present invention may be implemented in numerous ways within the spirit and scope of the present invention. Referring to FIG. 4, another embodiment of the redundant temperature monitoring system is illustrated. The system 400 of FIG. 4 includes a temperature sensor 402, first and second temperature measurement circuits 404, 410 and control circuit 406. Here, the first and second temperature measurement circuits 404, 410 simultaneously read the same, single temperature sensor 402. The system 400 uses less space at the measuring point due to its single temperature sensor and requires less wiring, therefore, simplifying the system 400.

Figure 5:
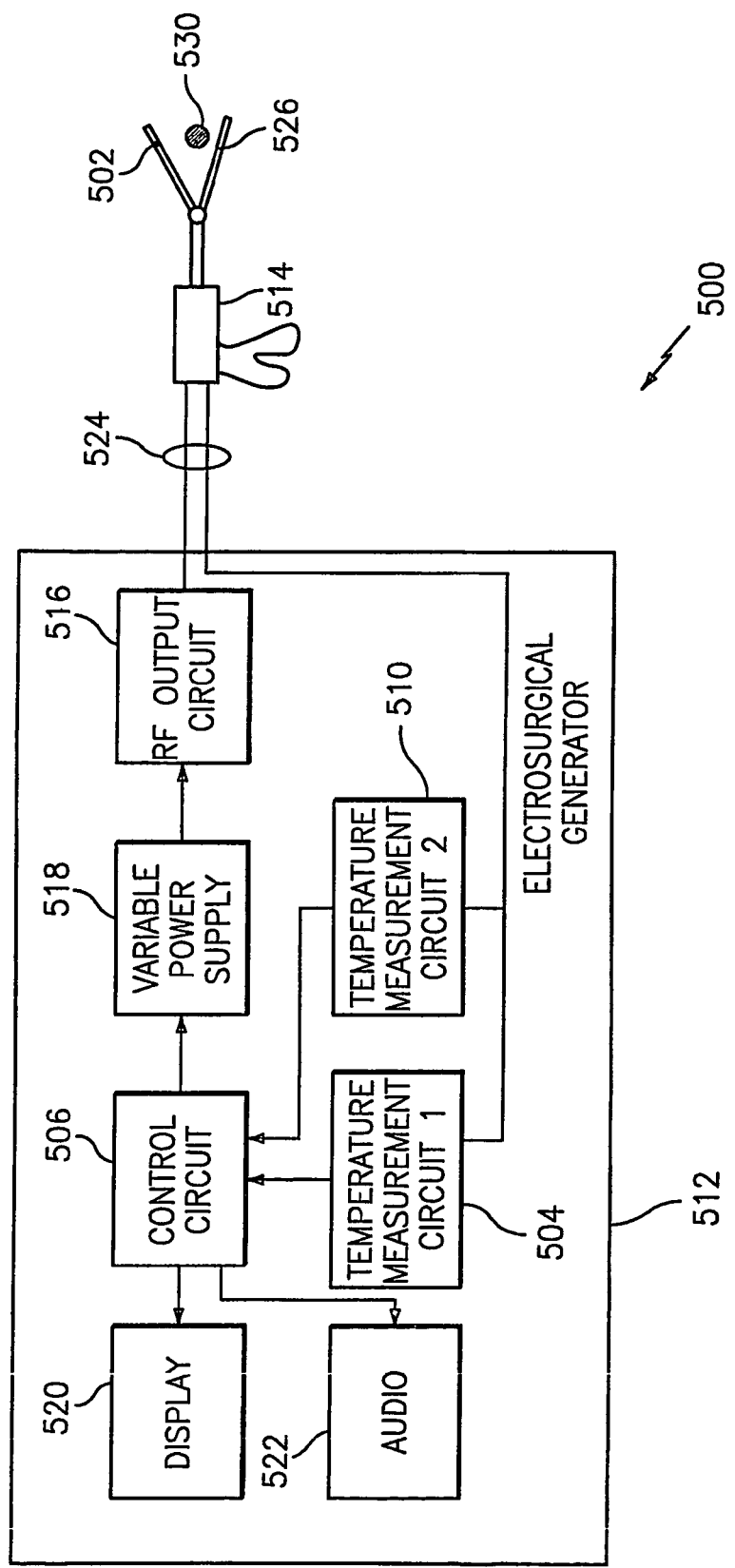
FIG. 5 is an exemplary electrosurgical system employing a redundant temperature monitoring system in accordance with the present invention.

An exemplary electrosurgical system 500 employing a redundant temperature monitoring system in accordance with the present invention is shown in FIG. 5. The system 500 can be used for sealing vessels 530 and other tissues of a patient, including ducts, veins, arteries and vascular tissue. The system 500 includes an electrosurgical generator 512 and a surgical instrument 514. The surgical instrument 514 is illustrated by way of example, and as will become apparent from the discussion below, other instruments can be utilized. The electrosurgical generator 512 includes several interconnected sub-units, including an RF output circuit 516, a control circuit 506, a variable D.C. power supply 518 and first and second temperature measurement circuits 504, 510. It is to be understood that the control circuit 506 controls the overall functions of the electrosurgical generator 512, in addition, to determining the difference of the first and second temperature values and comparing the difference to the plurality of thresholds. In other embodiments, a separate control circuit may be provided to perform the determining and comparing functions with its result being sent to another separate control circuit for controlling the overall functions of the electrosurgical generator.

Additionally, the electrosurgical generator 512 may include a display 520 for displaying temperature values, output power values, alarms, etc. The display 520 may take the form of LEDs, a liquid crystal display or any known display in the art. Furthermore, the electrosurgical generator may include an audio output 522, such as a speaker, for alerting a user, who for example may be performing a procedure an a patient and not observing the display.

The surgical instrument 514 is electrically connected to the electrosurgical generator 512 via cable 524 for receiving controlled electrosurgical power therefrom. The surgical instrument 514 has some type of end effector member 526, such as a forceps or hemostat, capable of grasping and holding the vessels and tissues of the patient. The member 526, also referred to simply as end effector 526, is assumed, in this embodiment, to be capable of applying and maintaining a relatively constant level of pressure on the vessel 530.

The member 526 is provided in the form of bipolar electrosurgical forceps using two generally opposing electrodes disposed on inner opposing surfaces of the member 526, and which are both electrically coupled to the output of the electrosurgical generator 512. During use, different electric potentials are applied to each electrode. Since tissue is an electrical conductor, the electrical energy output from the electrosurgical generator 512 is transferred through the intervening tissue. Both open surgical procedures and endoscopic surgical procedures can be performed with suitably adapted surgical instruments 514. It should also be noted that the member 526 could be monopolar forceps that utilizes one active electrode, with the other (return) electrode or pad being attached externally to the patient, or a combination of bipolar and monopolar forceps.

Temperature sensor 502 is preferably located in member 526 to measure the temperature of the patient tissue or of the operative site. In the embodiment shown in FIG. 5, one temperature sensor 502 is coupled to the first and second temperature measurement circuits 504, 510. In further embodiments, a temperature sensor may be provided for each temperature measurement circuit. The redundant temperature sensors at be positioned at the same location or one may be positioned in each end member 526.

The temperature sensor 502 is coupled to the temperature measurement circuits 504, 510 via cable 524. An output signal indicative of the temperature at the temperature sensor 502 is sent to the control circuit 506 from each of the first and second temperature measurement circuits 504, 510. The control circuit 506 then determines the difference between the first and second temperature values. The difference is then compared to a plurality of thresholds. If the difference is greater than a first predetermined threshold, the control circuit 506 generates a warning signal to be displayed on the display 520 and/or audibly produced at the audio output 522.

If the difference is greater than a second predetermined output, the control circuit 506 generates an alarm signal to be displayed on the display 520 and/or audibly produced at the audio output 522. Additionally, the control circuit 506 either shuts down the power supply 518 to effectively stop power from being output to the surgical tool 514 or adjust the output power to a lower level.

It is to be appreciated that output power from the electrosurgical generator can be adjusted in several ways. For example, the amplitude of the output power can be adjusted. In another example, the output power can be adjusted by changing the duty cycle or the crest factor.

In another embodiment, it is contemplated that the control circuit 506 controls a module for producing resistive heat for regulating heat applied to the tissue for achieving a desired tissue effect instead of or in addition to controlling the electrosurgical output circuit 516 and/or the power supply 518. The control circuit 506 responds to sensed tissue temperature indicative of tissue temperature and outputs a command signal for controlling output heat resistivity. Preferably, the module for producing resistive heat includes a current source and/or a variable resistor which are responsive to the command signal for outputting a desired current or providing a desired resistance, respectively. In this embodiment, if the temperature difference is greater than the second predetermined threshold, the control circuit 506 will control the module for producing resistive heat.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A temperature monitoring circuit for use with a power source comprising:
   at least one temperature sensor for sensing a temperature at a measuring point;
   a first temperature measurement circuit coupled to the at least one temperature sensor for generating a first temperature value;
   a second temperature measurement circuit coupled to the at least one temperature sensor for generating a second temperature value; and
   a control circuit configured to receive the first and second temperature values and programmed to determine a difference between the first and second temperature values when compared to each other and programmed to compare the difference to a first predetermined threshold,
   wherein the control circuit is configured to control the overall function of the power source.

2. The temperature monitoring circuit of claim 1, wherein, if the difference is greater than the first predetermined threshold, the control circuit generates a warning signal.

3. The temperature monitoring circuit of claim 1, wherein the control circuit is adapted to compare the difference to a second predetermined threshold and, if the difference is greater than the second predetermined threshold, the control circuit generates an alarm signal.

4. The temperature monitoring circuit of claim 1, wherein the control circuit is adapted to compare the difference to a second predetermined threshold and, if the difference is greater than the second predetermined threshold, the control circuit shuts down a power source.

5. The temperature monitoring circuit of claim 1, wherein the at least one temperature sensor is at least one of a thermocouple, thermistor, and resistance temperature detector.

6. The temperature monitoring circuit of claim 1, wherein the control circuit is at least one of a microprocessor, field-programmable gate array and programmable logic device.

7. The temperature monitoring circuit of claim 1, further comprising a second temperature sensor coupled to the second temperature measurement circuit.

8. An electrosurgical generator comprising:
   a radio frequency (RF) output circuit for outputting RF energy;
   a control circuit for controlling the output of the RF output circuit; and
   a temperature monitoring circuit comprising;
   at least one temperature sensor for sensing a temperature at a measuring point;
   a first temperature measurement circuit coupled to the at least one temperature sensor for generating a first temperature value;
   a second temperature measurement circuit coupled to the at least one temperature sensor for generating a second temperature value; and
   a control circuit configured to receive the first and second temperature values and programmed to determine a difference between the first and second temperature values when compared to each other and programmed to compare the difference to a first predetermined threshold,
   wherein the control circuit is configured to control the overall function of the electrosurgical generator.

9. The electrosurgical generator of claim 8, wherein, if the difference is greater than the first predetermined threshold, the control circuit generates a warning signal.

10. The electrosurgical generator of claim 9, further comprising a display for displaying the warning signal.

11. The electrosurgical generator of claim 9, further comprising an audio output for audibly producing the warning signal.

12. The electrosurgical generator of claim 8, wherein the control circuit is adapted to compare the difference to a second predetermined threshold and, if the difference is greater than the second predetermined threshold, the control circuit generates an alarm signal.

13. The electrosurgical generator of claim 12, further comprising a display for displaying the alarm signal.

14. The electrosurgical generator of claim 12, further comprising an audio output for audibly producing the alarm signal.

15. The electrosurgical generator of claim 8, wherein the control circuit is adapted to compare the difference to a second predetermined threshold and, if the difference is greater than the second predetermined threshold, the control circuit shuts down the RF output circuit.

16. The electrosurgical generator of claim 8, wherein the at least one temperature sensor is at least one of a thermocouple, thermistor, and resistance temperature detector.

17. The electrosurgical generator of claim 8, wherein the control circuit is at least one of a microprocessor, field-programmable gate array and programmable logic device.

18. The electrosurgical generator of claim 8, further comprising a second temperature sensor coupled to the second temperature measurement circuit.

19. An electrosurgical system comprising:
   an electrosurgical generator for outputting radio frequency (RF) energy;
   an electrosurgical instrument coupled to the electrosurgical generator for applying the RF energy to an operative site; and a temperature monitoring circuit comprising:
at least one temperature sensor for sensing a temperature at a measuring point;
a first temperature measurement circuit coupled to the at least one temperature sensor for generating a first temperature value;
a second temperature measurement circuit coupled to the at least one temperature sensor for generating a second temperature value; and
a control circuit configured to receive the first and second temperature values and programmed to determine a difference between the first and second temperature values when compared to each other and programmed to compare the difference to a first predetermined threshold,
wherein the control circuit is configured to control the overall function of the electrosurgical generator.

20. The electrosurgical system of claim 19, wherein the electrosurgical instrument comprises as least one end effector member and the at least one temperature sensor is located in the at least one end effector member.

21. The electrosurgical system of claim 19, wherein, if the difference is greater than the first predetermined threshold, the control circuit generates a warning signal.

22. The electrosurgical system of claim 21, wherein the electrosurgical generator further comprises a display for displaying the warning signal.

23. The electrosurgical system of claim 21, wherein the electrosurgical generator further comprises an audio output for audibly producing the warning signal.

24. The electrosurgical system of claim 19, wherein the control circuit is adapted to compare the difference to a second predetermined threshold and, if the difference is greater than the second predetermined threshold, the control circuit generates an alarm signal.

25. The electrosurgical system of claim 24, wherein the electrosurgical generator further comprises a display for displaying the alarm signal.

26. The electrosurgical system of claim 24, wherein the electrosurgical generator further comprises an audio output for audibly producing the alarm signal.

27. The electrosurgical system of claim 19, wherein the control circuit is adapted to compare the difference to a second predetermined threshold and, if the difference is greater than the second predetermined threshold, the control circuit shuts down a RF output circuit of the electrosurgical generator.

28. A method for controlling an electrosurgical system, the method comprising the steps of:
reading a first temperature value at an operative site via a first temperature circuit operably associated with an electrosurgical system including an electrosurgical generator;
reading a second temperature value at the operative site via a second temperature circuit operably associated with the electrosurgical system;
outputting the first and second temperature values to a control circuit operably associated with the electrosurgical system, the control circuit programmed to determine a difference between the first and second temperature values when compared to each other and programmed to compare the difference to a first predetermined threshold;
determining a difference of the first and second temperature values via the control circuit, wherein the control circuit is configured to control the overall function of the electrosurgical generator;
determining if the difference is greater than the first predetermined threshold, the first predetermined threshold indicative of a minimum allowable deviation between the first and second temperature values, wherein when the difference is greater than the first predetermined threshold, generating a warning signal.

29. The method as in claim 28, further comprising the step of, wherein when the difference is greater than a second predetermined threshold, the second predetermined threshold indicative of a maximum allowable deviation between the first an second temperature values, generating an alarm signal.

30. The method as in claim 28, further comprising the step of shutting down the electrosurgical system when the difference is greater than a second predetermined threshold.

* * * * *